(12) United States Patent
Knasiak

(10) Patent No.: US 7,033,562 B2
(45) Date of Patent: Apr. 25, 2006

(54) AMMONIA RECOVERY IN THE PREPARATION OF SILAZANES AND POLYSILAZANES

(75) Inventor: Gary Knasiak, Chalfont, PA (US)

(73) Assignee: Kion Corporation, Huntingdon Valley, PA (US)

( * ) Notice: Subject to any disclaimer, the term of this patent is extended or adjusted under 35 U.S.C. 154(b) by 303 days.

(21) Appl. No.: 10/685,689

(22) Filed: Oct. 14, 2003

(65) Prior Publication Data

US 2004/0076573 A1    Apr. 22, 2004

Related U.S. Application Data

(60) Provisional application No. 60/418,939, filed on Oct. 16, 2002.

(51) Int. Cl.
  *C01C 1/00*    (2006.01)
  *C01C 1/16*    (2006.01)
(52) U.S. Cl. .................. 423/352; 423/356; 423/470; 423/471; 423/499.4; 423/499.5
(58) Field of Classification Search ............. 423/352, 423/356, 470, 471, 499.4, 499.5
See application file for complete search history.

(56) References Cited

U.S. PATENT DOCUMENTS

| | | | | |
|---|---|---|---|---|
| 4,713,231 A | * | 12/1987 | Campbell et al. | 423/356 |
| 5,196,556 A | * | 3/1993 | Vaahs et al. | 556/409 |
| 5,281,318 A | | 1/1994 | Tahara | |
| 5,746,993 A | * | 5/1998 | Mullee | 423/352 |
| 6,329,487 B1 | | 12/2001 | Abel et al. | 528/21 |
| 2002/0165319 A1 | | 11/2002 | Knasiak et al. | |

* cited by examiner

*Primary Examiner*—Stanley S. Silverman
*Assistant Examiner*—Maribel Medina

(57) ABSTRACT

Silazanes and/or polysilazanes are prepared by ammonolysis reaction in liquid anhydrous ammonia by introducing at least one halosilane into the ammonia. In addition to the silazane and/or polysilazane, an ammonolysis by-product also results. A substantially more efficient process is disclosed for treating the by-product through the addition of a liquid, namely water, or a solution comprising a strong base, or an aqueous acid solution. The process may be employed for more efficient, economical recovery of ammonia from such waste stream solutions of ammonia halide, or acids thereof for use as recycle in the further production of silazanes and polysilazanes, and/or for producing a less hazardous, more readily disposable salt residue thereof.

22 Claims, No Drawings

AMMONIA RECOVERY IN THE PREPARATION OF SILAZANES AND POLYSILAZANES

CROSS REFERENCE TO RELATED APPLICATION

This application claims the benefit of U.S. Provisional Application 60/418,939, filed Oct. 16, 2002.

TECHNICAL FIELD

This invention relates generally to an ammonia recovery process, and more specifically, to a substantially more efficient process for recovering liquid, anhydrous ammonia, including environmentally less hazardous, more readily disposable salt by-products all in the manufacture of silazanes and polysilazanes.

BACKGROUND OF THE INVENTION

U.S. Pat. No. 6,329,487 to Abel et al discloses a process for preparing novel silazanes and polysilazanes by ammonolysis of a chlorosilane, for example, or a mixture of chlorosilanes comprising the addition of these chlorosilanes to liquid anhydrous ammonia. There are many advantages to such a process over other processes in preparing silazanes and polysilazanes, as detailed by Abel et al.

A disadvantage of this process, however, resides in the handling and/or disposal of the solution of ammonium halide in liquid anhydrous ammonia, which results as a by-product of the reaction. On the one hand, the ammonium halide solution can be dealt with by simply evaporating the liquid anhydrous ammonia from the solution to leave dry, ammonium halide salt. The ammonia gas which results can be recovered and recondensed back to liquid form and reused in the process.

While the above ammonia recovery process is attractive from an economical standpoint, it was found that a great deal of the ammonia originally introduced in the process is lost as ammonium halide salt. It is believed that the problem with simply allowing the ammonia to evaporate is due, at least in part, to the problem associated with the ammonium halide salt which precipitates out of solution in the process. To wit, as the ammonia evaporates from the solution of solubilized and ionized ammonium halide salt in liquid ammonia the concentration of the ammonium halide salt increases. As the concentration of the salt increases during evaporation the adsorption of residual ammonia onto the precipitated solid salt increases, resulting in physical entrapment of residual liquid anhydrous ammonia within the solid ammonium halide salt. This encumbers evaporation and recovery of the ammonia from the solution of ammonium halide salt in liquid anhydrous ammonia. Additionally, the problem of waste disposal of the ammonium halide salt remains, so that environmental concerns are not addressed as fully as one would desire.

Accordingly, there is a need for a more efficient process for the recovery of ammonia from an ammonolysis reaction in the production of silazanes and polysilazanes, and one that results in a less hazardous, more readily disposable salt residue.

SUMMARY OF THE INVENTION

It has now been discovered that the addition of a liquid, namely water, a solution comprising a strong base, such as an alkali metal hydroxide or a solution comprising an acid, such as an organic acid, like acetic acid, or a mineral acid, like sulfuric acid are useful in treating by-product solutions, especially solubilized and ionized solutions of ammonium halide salt in liquid anhydrous ammonia produced during ammonolysis reactions in the synthesis of silazanes and polysilazanes.

It is therefore a principal object of the invention to provide an improved process which offers the advantages of: (i) more efficient, economical recovery of ammonia from waste stream solutions of ammonium halide in liquid anhydrous ammonia, than otherwise achieved through ordinary evaporation processes, and as a further embodiment of the invention (ii) one which also allows for the conversion of ammonium halide salts to more environmentally friendly salt residues, such as sodium chloride, for non-hazardous waste removal.

For purposes of this invention, the following terms and expressions as appearing in the specification and claims are intended to have the following meanings:

"Ammonolysis" or "ammonolysis reaction" or variations thereof mean processes and methods for the production of silazanes and/or polysilazanes wherein a halosilane reacts with liquid anhydrous ammonia and yields, in addition to the silazane and/or polysilazane, a by-product comprising at least an ammonium halide salt in anhydrous liquid ammonia. One representative example of an ammonolysis reaction for the production of silazanes and polysilazanes intended under this invention is disclosed by U.S. Pat. No. 6,329,487 (Abel et al). It is to be understood, however, the terms and expressions "ammonolysis" or "ammonolysis reaction" or variations thereof are not intended to be limited only to the products and processes disclosed by Abel et al, but include all other such processes and methods for the production of silazanes and polysilazanes, wherein more efficient recovery of ammonia and/or treatment of the accompanying salt from a salt/ammonia containing by-product would be desirable.

"Silazane" and "polysilazane", as appearing in the specification and claims are generic terms intended to include monomers, oligomers, cyclic, polycyclic, linear polymers or resinous polymers having at least one Si—N group in the compound. Included are such representative ammonolysis products generally known among persons skilled in the art as: silazanes, disilazanes, polysilazanes, polysiloxazanes, ureasilazanes, polyureasilazanes, aminosilanes, organosilazanes, organopolysilazanes, inorganic polysilazanes, and others employing liquid anhydrous ammonia in their production.

Accordingly, it is a further object of the invention to provide a process for treating a by-product generated in an ammonolysis reaction for the production of a silazane and/or polysilazane product by the steps, which comprise:

(i) separating the silazane and/or polysilazane product from an ammonolysis by-product comprising at least one ammonium halide salt or acid thereof in anhydrous liquid ammonia;

(ii) forming a reaction mixture by introducing into the by-product a liquid selected from the group consisting of water, a solution comprising a strong base or an acid, and (iii) reacting the reaction mixture resulting in a solution comprising at least ammonium hydroxide and a metal halide salt and/or an ammonium halide salt.

The foregoing process will usually be practiced wherein the ammonium halide salt or acid thereof of the ammonolysis by-product of step (i) is solubilized and ionized in the anhydrous liquid ammonia.

It is yet a further principal object of the invention to provide an improved process for treating by-product mixtures resulting from the production of useful silazanes and/or polysilazanes, like those of U.S. Pat. No. 6,329,487 (Abel et al), wherein the silazane or polysilazane product is one which is prepared by an ammonolysis reaction in liquid anhydrous ammonia by introducing at least one halosilane into the liquid anhydrous ammonia. The amount of liquid anhydrous ammonia is at least twice the stoichiometric amount of silicon-halide bonds on the halosilane. In their production, the halosilane reacts with the anhydrous liquid ammonia to form an ammonolysis product which is a silazane or polysilazane and an ammonium halide salt or acid thereof. The ammonium halide salt or acid is solubilized and ionized in the liquid anhydrous ammonia.

In one aspect of the present invention, a reaction mixture is formed comprising the ammonolysis by-product, for example, solubilized and ionized ammonium halide salt in liquid anhydrous ammonia mixed with a sufficient amount of water. This reaction mixture then reacts converting the liquid anhydrous ammonia to a solution comprising, for example, ammonium hydroxide and an ammonium halide salt. Compositionally, this solution is more suitable for nonhazardous waste removal than the original ammonolysis by-product solution. In addition, as will be discussed in greater detail below, this solution can also be treated for recovery of the ammonia values for recycle in the production of silazanes and polysilazanes, for example.

A further aspect of the invention allows for the alternative embodiment wherein the recovery of ammonia might also be viewed as less important, in which case the ammonolysis by-product comprising the at least one ammonium halide salt or acid thereof in liquid anhydrous ammonia can be converted to an environmentally less or nonhazardous material for waste removal. In such case, the ammonolysis by-product may also be reacted with a sufficient amount of a solution of a base, such as an alkali metal hydroxide to convert substantially all the ammonium halide salt of the ammonolysis by-product to a solution comprising an alkali metal halide and ammonium hydroxide. Such a solution comprising salts like sodium chloride are environmentally more friendly than the untreated ammonolysis by-product. The pH of such treated solutions generally range from about 8 to about 11. As noted above in connection with aqueous reaction mixtures, the solutions of this embodiment of the invention also comprising ammonium hydroxide may be treated for recovery of ammonia values for recycle.

In a similar manner, the process of converting the ammonolysis by-product to an environmentally more acceptable by-product for nonhazardous waste removal can be performed by introducing a sufficient amount of an acid, such as an organic acid, to convert the ammonium halide salt to an ammonium salt of the acid and adjust the pH of the reaction mixture to range generally from about 6 to about 10.

It is, however, the principal objective of the invention to provide a more efficient, and therefore, more economic aqueous process for full, or substantially a 100 percent recovery of ammonia from the ammonolysis by-product from the production of silazanes and/or polysilazanes. The recovered ammonia may be recycled for further use in the production of such products. Typically, the process provides for introducing water into the reaction mixture, preferably in a solubilized and ionized state in the liquid anhydrous ammonia, and in a further step (iv) removing or stripping the ammonia from the reaction mixture (iii) by known methods for further processing. This may include recovery of the ammonia as a vapor under reduced pressure, condensing the vapor, and storing as liquid anhydrous ammonia for recycling in the production of new silazanes and/or polysilazanes.

DESCRIPTION OF THE PREFERRED EMBODIMENTS

Silazanes and/or polysilazanes prepared by ammonolysis reaction are wide and varied, as previously indicated, and so the ammonolysis by-products of this invention will also vary widely.

Compositionally, the by-product of an ammonolysis reaction in the preparation of a silazane and/or polysilazane will comprise liquid anhydrous ammonia with at least one ammonium halide salt, such as ammonium chloride and ammonium bromide, as representative examples, or acid thereof.

The present invention has been found to be especially useful in treating the ammonolysis by-product from the production of silazanes and/or polysilazanes of Abel et al as disclosed in U.S. Pat. No. 6,329,487, the contents of which are hereby incorporated by reference herein.

The silazanes/polysilazanes of Abel et al are characterized by repeating units of silicon-nitrogen linkages having a reduced number of Si—H bonds relative to the amount of Si—H bonds contained in a halosilane starting compound used to prepare the polysilazanes. That is to say, the polysilazanes comprise a reduced amount of Si—H bonds relative to the quantity of Si—H bonds incorporated into the polysilazane from a starting compound comprising at least one Si—H bond and at least one Si-halide bond, the polysilazane further comprising a greater number of Si—N bonds and a greater nitrogen content than would otherwise be derived from complete ammonolysis of the Si-halide bonds of the starting compound. The reduction in Si—H bonds can range from about 10% to about 90% relative to the number of Si—H bonds contained in the starting compounds. Additionally, it has been found there is a proportional increase in the Si—N linkages which is essentially proportional to the reduction in Si—H bonds. The preferred polysilazanes comprise several different structures including linear, branched, ladder, and fused ring morphologies, although it is believed that these polysilazanes have fewer isolated ring structures than earlier polysilazanes.

Representative examples of polysilazanes having fused six and eight membered rings are shown in structures (1) and (2) below. These structures are merely representative of the polysilazanes prepared with the halosilanes employing the methods disclosed in U.S. Pat. No. 6,329,487, wherein R is independently selected from the group consisting of hydrogen, substituted or unsubstituted alkyl, substituted or unsubstituted cycloalkyl, substituted or unsubstituted alkenyl or substituted or unsubstituted aryl group, and n is 1 or greater.

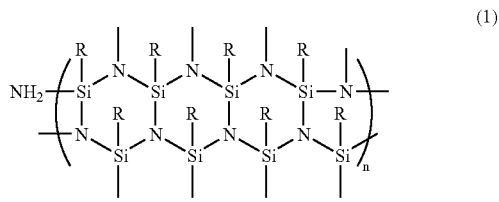

(1)

-continued

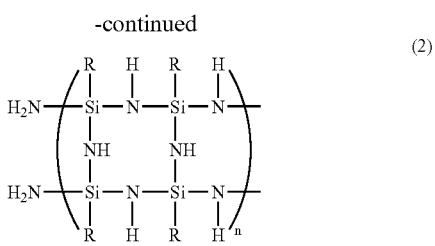

(2)

It is believed that the initial reaction leading to the formation of the ammonolysis products of Abel, et al may be represented generally by the following scheme showing a possible mechanistic route using a Si—H bond containing starting compound, such as methyldichlorosilane:

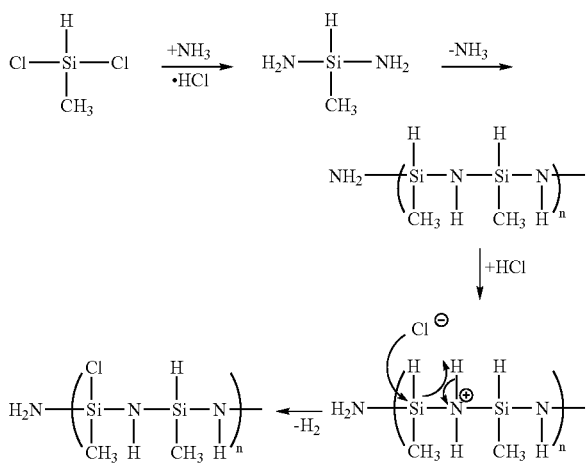

During the initial ammonolysis, the silicon-chlorine bonds undergo ammonolysis, generating a diaminosilane which is further converted into a linear molecule containing several Si—N repeat units. The linear structure is stabilized in the anhydrous liquid ammonia containing an ionized ammonium halide salt dissolved therein. This ionized and dissolved ammonium halide salt then acts as an acid catalyst which catalyzes a loss of a Si—H bond to generate a new silicon-chlorine bond on the straight chain of the polymer. The newly generated chlorosilane bond may then undergo further ammonolysis. This reaction will proceed until virtually all chlorosilicon bonds undergo ammonolysis.

The polymerization can be performed in the same reactor and at the same conditions used for ammonolysis and without isolation of the initial silazane ammonolysis product. Thus, ammonolysis and polymerization may all be occurring at the same time. Two easily-separated phases are formed and the polysilazane can be easily isolated in a relatively pure state as one of the two liquid phases. Such polysilazanes are also commercially available under the Registered trademark "KION" from the KION Corporation, Huntington Valley, Pa., 19006, USA.

The distinct second phase of the above reaction comprises the by-products of the ammonolysis reaction, including an ammonium halide salt or acid thereof solubilized and ionized in the liquid anhydrous ammonia. When under pressure and at room temperature the salt remains in solution. However, to recover the ammonia by evaporation the pressure in the closed vessel is reduced to allow the ammonia to evaporate. In practicing the methods of the present invention, a sufficient amount of water, for example, is introduced into the vessel to keep the ammonium halide, e.g., chloride salt, in solution. This facilitates stripping the ammonia from the ammonolysis by-product making the removal and recovery of substantially all of the ammonia a more efficient process, as will be demonstrated in greater detail below.

As a further feature, when water is added to the ammonolysis by-product containing the solubilized and ionized ammonium halide salt solution in liquid anhydrous ammonia, a solution of ammonium halide salt in aqueous ammonium hydroxide is formed. This is a buffered solution with a pH value which is neither strongly basic nor strongly acidic, typically in a range from about 10 to about 10.5. Therefore, after removal of the ammonia and further processing for recycling by methods known in the art the remaining solution containing ammonium halide salt may be more readily disposed of as a nonhazardous material, and in some instances depending on local regulations, may even be disposed of using standard municipal waste disposal systems.

In sum, it has been discovered that the recovery of ammonia from the ammonolysis by-product solution according to the subject concept of this invention by equilibrative evaporation is faster, more efficient and more complete than the recovery of an equivalent quantity of ammonia from the solution of solubilized and ionized ammonium halide in the liquid anhydrous ammonia which is present before the addition of water. Hence, the efficiency of the process is increased, since the recovery time is reduced.

As previously indicated, it is thought that this kinetic recovery efficiency relative to a simple evaporative recovery of the liquid anhydrous ammonia is due, in part, to the problem associated with the evaporation of liquid anhydrous ammonia from the precipitated, solid ammonium halide salt which results when ammonia is simply evaporated from a solution of solubilized and ionized ammonium halide salt in liquid ammonia. In such a recovery process, as the concentration of the ammonium halide salt increases during evaporation, the adsorption onto the ammonium halide salt, and physical entrapment of residual liquid anhydrous ammonia within the solid ammonium halide salt present impedes the rate of evaporation. With the introduction of water, however, the ammonium halide salt remains dissolved in the water as the ammonia evaporates from the solution, providing for efficient mixing and separation.

When aqueous solutions of a base, such as an alkali metal hydroxide, e.g., aqueous solution of sodium or potassium hydroxide, are introduced into the ammonolysis by-product comprising solubilized and ionized ammonium halide salt solution in liquid anhydrous ammonia, the alkali metal hydroxide undergoes a chemical reaction with the ammonium halide salt to form alkali metal halide salt and ammonium hydroxide. This results in an aqueous solution containing both ammonium hydroxide and alkali metal halide. Again, this mixture, depending on local government regulations, may be disposed of using standard municipal waste disposal systems, and/or also be subjected to evaporative ammonia recovery, as described above. When this later method is used, the highly efficient ammonia recovery leaves behind a substantially pure, aqueous solution of the alkali metal halide in water.

A particularly preferred embodiment utilizes an aqueous solution of sodium hydroxide as the alkali metal hydroxide, although potassium hydroxide is also suitable. A sufficient amount of the aqueous base is added to fully convert the ammonium halide salt in the ammonolysis by-product to the more enviromentally friendly alkali metal halide. Thus, when sodium hydroxide is used, for instance, the aqueous solution of this base reacts with the ammonium halide converting it to sodium chloride in water. "Salt water" of this composition may, depending on local regulations, be disposed of using standard municipal waste disposal systems. If a pH closer to 7 is required, it may be modified with an aqueous solution of acid to adjust the pH to such a lower value.

As a further alternative embodiment, the invention may also be practiced employing an acid, instead of a base or water. While weak organic acids, such as solutions of acetic, propanoic or oxalic acids are generally preferred, the invention may also be practiced using aqueous solutions of mineral acids, such as sulfuric and hydrochloric acids. The ammonolysis by-product containing alkali metal halide or acid thereof in liquid anhydrous ammonia typically having a pH of approximately 10 can be treated with a sufficient amount of the acid to neutralize the solution. In the case of acetic acid, the acid converts the ammonium halide and anhydrous liquid ammonia to ammonium acetate. Alternatively, the invention can also be practiced with lesser amounts of acid, in which case ammonia can also be recovered, such as by reducing the pressure in the vessel to allow the ammonia to evaporate.

In order to more fully demonstrate the various aspects of the invention the following experiments were performed:

EXAMPLE 1

Part A Aqueous Process with Full Evaporative Ammonia Recovery 11.71 kilograms of a polysilazane were prepared by the ammonolysis of a mixture consisting of 80 wt % methyldichlorosilane and 20 wt % vinylmethyldichlorosilane according to the procedure described in Example 1 of U.S. Pat. No. 6,329,487. The ammonolysis was conducted at pressure levels which varied between 30 psia and 130 psia as the dichlorosilane mixture was injected into the liquid ammonia and reacted with the liquid ammonia. When the reaction was complete, the pressure in the reactor was 70 psia, and two separate liquid layers, as described in the example, were observed to form. The polysilazane product was obtained as the lower layer, while the solution of ammonium chloride in liquid anhydrous ammonia was obtained as the upper layer. The polysilazane layer was then separated from the layer containing the dissolved ammonium chloride by-product in the liquid anhydrous ammonia at a pressure of 70 psia. The reaction resulted in 59.42 liters of a solution of ammonium chloride in liquid anhydrous ammonia which had a pH of 10.47 and weighed 53.48 kilograms. The solution contained 33.90 kilograms of liquid anhydrous ammonia and 19.58 kilograms of ammonium chloride (36.6% ammonium chloride concentration). This solution was then charged at a pressure which varied between 65 psia and 80 psia to a 212 liter capacity jacketed paddle tumbler manufactured by American Process Systems, Eirich Machines, Inc., 4033 Ryan Road, Gurnee, Ill. 60031). 19 liters of water were then charged to the tumbler at a pressure of 100 psia, after which tumbling and steam heating of the tumbler was initiated. The gaseous ammonia which evolved was recondensed to liquid anhydrous ammonia as it evolved. After 1.0 hour an additional 19 liters of water were added to the tumbler at a pressure of 100 psia and gaseous ammonia stripping of the aqueous solution was continued. After 2 hours, a final aliquot of 19 liters of water was added. When approximately 90% of the total ammonia content of the solution was recovered as liquid anhydrous ammonia (30.51 kilograms) a significant pressure drop in the tumbler was observed. Gaseous ammonia evaporation from the aqueous solution was continued, and was found to be complete at the end of only 3 hours.

This compares favorably to the 7 hours required to recover the same amount of ammonia in the identical reaction as described in Comparative Example B below, wherein water was not added to the solution of ammonium chloride in liquid anhydrous ammonia. A total of 33.0 kilograms of liquid anhydrous ammonia were recovered by recondensation of the evaporated ammonia, and an aqueous solution of ammonium chloride remained in the tumbler. The recovered liquid anhydrous ammonia was found to contain less than 0.1% residual water, enabling its reuse in subsequent polysilazane preparations. The aqueous solution of ammonium chloride had a pH of 6 and was reserved for non-hazardous waste removal.

Part B Comparative Example: Non-Aqueous Process with Full (100%) Evaporative Ammonia Recovery Example 1, Part A was repeated, except that no water was added to the tumbler during the evaporation of the ammonia. A total of 19.5 kilograms of dry ammonium chloride salt and 33.0 kilograms of liquid anhydrous ammonia were recovered. However, the evaporation and recondensation of the liquid anhydrous ammonia required a total time of 7 hours, resulting in both time and energy inefficiencies compared to Part A of Example 1.

EXAMPLE 2

Aqueous Process with no Evaporative Ammonia Recovery

A) Example 1 was repeated, but instead of recovering the ammonia by evaporation and recondensation, 112 kilograms of water were simply added slowly to the tumbler containing the by-product solution of ammonium chloride in liquid anhydrous ammonia. The resulting buffered aqueous solution of ammonium hydroxide and ammonium chloride had a pH of 10.34. The solution was retained for nonhazardous waste removal.

B) Example 1 was repeated, but instead of recovering the ammonia by evaporation and recondensation, 84 kilograms of water were simply added slowly to the tumbler containing the by-product solution of ammonium chloride in liquid anhydrous ammonia. The resulting buffered aqueous solution of ammonium hydroxide and ammonium chloride had a pH of 10.37. The solution was retained for nonhazardous waste removal.

C) Example 1 was repeated, but instead of recovering the ammonia by evaporation and recondensation, 70 kilograms of water were simply added slowly to the tumbler containing the by-product solution of ammonium chloride in liquid anhydrous ammonia. The resulting buffered aqueous solution of ammonium hydroxide and ammonium chloride had a pH of 10.40. The solution was retained for nonhazardous waste removal.

D) Example 1 was repeated, but instead of recovering the ammonia by evaporation and recondensation, 112 kilograms of 2.5% aqueous acetic acid were simply added slowly to the tumbler containing the by-product solution of ammonium chloride in liquid anhydrous ammonia. The resulting, buffered aqueous solution of ammonium hydroxide and ammonium chloride had a pH of 10.03. The solution was retained for nonhazardous waste removal.

E) Example 1 was repeated, but instead of recovering the ammonia by evaporation and recondensation, 27 kilograms of 5% aqueous acetic acid were simply added slowly to the tumbler containing the by-product solution of ammonium chloride in liquid anhydrous ammonia. The resulting buffered aqueous solution of ammonium hydroxide and ammonium chloride had a pH of 10.22. The solution was retained for nonhazardous waste removal.

F) Example 1 was repeated, but instead of recovering the ammonia by evaporation and recondensation, 70 kilograms of 1% aqueous acetic acid were simply added slowly to the tumbler containing the by-product solution of ammonium chloride in liquid anhydrous ammonia. The resulting buffered aqueous solution of ammonium hydroxide and ammonium chloride had a pH of 10.32. The solution was retained for nonhazardous waste removal.

G) Example 1 was repeated, but instead of recovering the ammonia by evaporation and recondensation, 59.78 kg of 6.2% aqueous sulfuric acid were slowly added to the tumbler containing the by-product solution of ammonium chloride in liquid anhydrous ammonia. The resulting buffered aqueous solution of ammonium hydroxide, ammonium chloride and ammonium sulfate had a pH of 10.44.

H) Example 1 was repeated, but instead of recovering the ammonia by evaporation and recondensation, 66.86 kg of 15.92% aqueous sulfuric acid were slowly added to the tumbler containing the by-product solution of ammonium chloride in liquid anhydrous ammonia. The resulting buffered aqueous solution of ammonium hydroxide, ammonium chloride and ammonium sulfate had a pH of 9.69.

I) Example 1 was repeated, but instead of recovering the ammonia by evaporation and recondensation, 69.80 kg of 19.38% aqueous sulfuric acid were slowly added to the tumbler containing the by-product solution of ammonium chloride in liquid anhydrous ammonia. The resulting buffered aqueous solution of ammonium hydroxide, ammonium chloride and ammonium sulfate had a pH of 8.84.

EXAMPLE 3

Aqueous Process with 75% Evaporative Ammonia Recovery

A pH-buffered aqueous solution of ammonium hydroxide and ammonium chloride was obtained as a waste product by repeating Example 1, but limiting the evaporation of ammonia from the solution by tumbler heating to the point where only 75% of the ammonia originally charged to the reactor was recovered. A pH-buffered solution of ammonium hydroxide and ammonium chloride at a pH of 9.6 was obtained. The buffered ammonium chloride/ammonium hydroxide solution was retained for nonhazardous waste removal.

EXAMPLE 4

Aqueous Process with 50% Evaporative Ammonia Recovery

A pH-buffered aqueous solution of ammonium hydroxide and ammonium chloride was obtained as a waste product by repeating Example 1, but limiting the evaporation of ammonia from the solution by tumbler heating to the point where only 50% of the ammonia originally charged to the reactor was recovered. A pH-buffered solution of ammonium hydroxide and ammonium chloride at pH 10.2 was obtained. The buffered ammonium chloride/ammonium hydroxide solution was retained for non-hazardous waste removal.

EXAMPLE 5

Aqueous Process with Reactive Recovery of Ammonia from the Ammonium Chloride by-Product via Sodium Hydroxide Addition Example 1 is repeated, except that instead of adding three, 19 liter portions of water, three, 19 liter portions of an aqueous, 5 Molar sodium hydroxide solution are carefully added to reactively disproportionate the ammonium chloride salt by-product during the process of ammonia evaporation and recovery. The total amount of liquid anhydrous ammonia recovered is 40.1 kilograms. Sodium chloride is obtained upon water evaporation.

I claim:

1. A process for treating a by-product generated in an ammonolysis reaction for the production of a silazane or polysilazane product, which comprises the steps of:
    (i) separating the silazane or polysilazane product from an ammonolysis by-product comprising at least one ammonium halide salt or acid thereof in liquid anhydrous ammonia;
    (ii) forming a reaction mixture by introducing into said ammonolysis by-product a liquid selected from the group consisting of water, a solution comprising a strong base and an acid, and
    (iii) reacting said reaction mixture resulting in a solution comprising at least ammonium hydroxide and a metal halide salt and/or ammonium halide salt.

2. The process according to claim 1, wherein the ammonium halide salt or acid thereof of the ammonolysis by-product of step (i) is solubilized and ionized in the liquid anhydrous ammonia.

3. The process according to claim 2, wherein the ammonolysis by-product is reacted with a sufficient amount of water to convert the anhydrous ammonia to a solution comprising at least ammonium hydroxide.

4. The process according to claim 3, including the further step of stripping and recovering ammonia from said solution comprising at least ammonium hydroxide.

5. The process according to claim 4, wherein the step of stripping and recovering ammonia from said solution comprising at least ammonium hydroxide results in a material comprising a buffered solution comprising at least an alkali metal halide salt.

6. The process according to claim 2, wherein the reaction mixture comprising the ammonolysis by-product is reacted with a strong base comprising an aqueous solution of an alkali metal hydroxide, said reaction mixture reacting to convert the ammonium halide salt to a solution comprising at least an alkali metal halide salt and ammonium hydroxide.

7. The process according to claim 6, wherein the aqueous solution of alkali metal hydroxide is sodium hydroxide or potassium hydroxide.

8. The process of claim 6, including the further step of stripping and recovering ammonia from the reaction mixture comprising said ammonium hydroxide.

9. The process according to claim 2, wherein the reaction mixture comprising the ammonolysis by-product is reacted with a sufficient amount of an aqueous acid to yield a product comprising at least an ammonium salt of the acid and to adjust the pH to a range from about 6 to about 10.

10. The process according to claim 9, wherein the acid is an organic acid or a mineral acid.

11. The process according to claim 10, wherein said organic acid is a member selected from the group consisting of acetic acid, propanoic acid and oxalic acid.

12. The process according to claim 10, wherein the mineral acid comprises hydrochloric acid or sulfuric acid.

13. The process according to claim 9, comprising the further step of recovering ammonia from the product of the reaction.

14. The process according to claim 2, comprising the steps of introducing water into the reaction mixture comprising the ammonolysis by-product, stripping ammonia from the reaction mixture, recovering the ammonia as a vapor and condensing as liquid anhydrous ammonia.

15. The process according to claim 14, wherein the step of stripping the ammonia from the reaction mixture is performed by heating.

16. The process according to claim 14, wherein the step of stripping the ammonia from the reaction mixture is performed by subjecting said mixture to reduced pressure.

17. The process according to claim 1, wherein the silazane or polysilazane product is one which is prepared by an ammonolysis reaction in liquid anhydrous ammonia by introducing at least one halosilane into said liquid anhydrous ammonia, the amount of liquid anhydrous ammonia being at least twice the stoichiometric amount of silicon-halide bonds on the halosilane, the halosilane reacting with the liquid anhydrous ammonia to form an ammonolysis product which is a silazane or polysilazane and an ammonium halide salt or acid thereof, the ammonium halide salt or acid thereof being solubilized and ionized in the liquid anhydrous ammonia.

18. The process according to claim 17, comprising the further step of separating ammonia from the mixture of water with the solubilized and ionized ammonium halide salt and liquid anhydrous ammonia.

19. The process according to claim 18, wherein the separation of ammonia from the mixture of water with the solubilized and ionized ammonium halide salt and liquid anhydrous ammonia is performed by heating.

20. The process according to claim 18, wherein the separation of ammonia from the mixture of water with the solubilized and ionized ammonium halide salt and liquid anhydrous ammonia is performed by subjecting the mixture to reduced pressure.

21. The process according to claim 20, wherein the ammonia which is separated from the mixture of water with the solubilized and ionized ammonium halide salt and liquid anhydrous ammonia is removed from the mixture as ammonia gas.

22. The process according to claim 20, comprising the further step of recondensing the removed ammonia gas to liquid anhydrous ammonia.

* * * * *

UNITED STATES PATENT AND TRADEMARK OFFICE
CERTIFICATE OF CORRECTION

PATENT NO.         : 7,033,562 B2
APPLICATION NO. : 10/685689
DATED              : April 25, 2006
INVENTOR(S)        : Gary Knasiak It is certified that error appears in the above-identified patent and that said Letters Patent is hereby corrected as shown below:

On the Title Page,
Item (74) Attorney, Agent, or Firm should read -- Howard M. Ellis Signed and Sealed this Seventeenth Day of October, 2006

JON W. DUDAS
*Director of the United States Patent and Trademark Office*